US012111260B2

(12) United States Patent
Mazina-Šinkar et al.

(10) Patent No.: US 12,111,260 B2
(45) Date of Patent: Oct. 8, 2024

(54) APPARATUS AND METHOD FOR DETERMINATION OF BANNED SUBSTANCES

(71) Applicant: TALLINN UNIVERSITY OF TECHNOLOGY, Tallinn (EE)

(72) Inventors: Jekaterina Mazina-Šinkar, Tallinn (EE); Jelena Gorbatšova, Tallinn (EE); Enn Erme, Tallinn (EE); Artur Abels, Tallinn (EE); Jaas Ježov, Tallinn (EE); Merike Vaher, Tallinn (EE); Mihkel Kaljurand, Tallinn (EE)

(73) Assignee: TALLINN UNIVERSITY OF TECHNOLOGY, Tallinn (EE)

( * ) Notice: Subject to any disclaimer, the term of this patent is extended or adjusted under 35 U.S.C. 154(b) by 247 days.

(21) Appl. No.: 17/682,404

(22) Filed: Feb. 28, 2022

(65) Prior Publication Data
US 2022/0178825 A1    Jun. 9, 2022

Related U.S. Application Data

(63) Continuation of application No. PCT/EP2020/074255, filed on Aug. 31, 2020.
(Continued)

(51) Int. Cl.
*G01N 21/64* (2006.01)
*G01N 1/10* (2006.01)
(Continued)

(52) U.S. Cl.
CPC .......... *G01N 21/6428* (2013.01); *G01N 1/10* (2013.01); *G01N 21/645* (2013.01);
(Continued)

(58) Field of Classification Search
CPC .... G01N 21/6428; G01N 1/10; G01N 21/645; G01N 33/946; G01N 33/948;
(Continued)

(56) References Cited

U.S. PATENT DOCUMENTS

| 5,246,577 A | 9/1993 | Fuchs et al. |
| 6,843,901 B1 * | 1/2005 | Li .................... G01N 27/4473 |
| | | 204/603 |

(Continued)

FOREIGN PATENT DOCUMENTS

| WO | 2005040331 A1 | 5/2005 |
| WO | 2014153099 A2 | 9/2014 |

(Continued)

OTHER PUBLICATIONS

International Search Report and Written Opinion issued in PCT/EP2020/074255, mailed Jul. 13, 2021, 17 pages.

*Primary Examiner* — Kiho Kim
(74) *Attorney, Agent, or Firm* — Meunier Carlin & Curfman LLC

(57) ABSTRACT

The present invention relates to roadside analyzer for determination of illegal drugs abuse, including, but not limiting to detection of explosives, toxic industrial chemicals and other banned or regulated compounds, biomarkers and phytochemicals in a sample in situ in at least one human body fluid sample, specifically in oral fluid (saliva), but not limiting to other clinical samples of interest (urine, blood, exhaled breath, exhaled breath condensate, etc.) It consists of automatic processor for preparing samples suitable for analysis. Analysis part of the instrument implements three technologies, namely solid phase extraction prior to analysis, capillary electrophoresis for separation of analytes from the sample matrix and impedance (contactless conductivity)

(Continued)

or fluorescence or both impedance (contactless conductivity) and fluorescence for detection of analytes of interest.

14 Claims, 7 Drawing Sheets

Related U.S. Application Data

(60) Provisional application No. 62/893,871, filed on Aug. 30, 2019.

(51) Int. Cl.
*G01N 33/94* (2006.01)
*G01N 1/02* (2006.01)

(52) U.S. Cl.
CPC ......... *G01N 33/946* (2013.01); *G01N 33/948* (2013.01); *G01N 33/9486* (2013.01); *G01N 2001/024* (2013.01)

(58) Field of Classification Search
CPC ......... G01N 33/9486; G01N 2001/024; G01N 27/44726; G01N 27/4473; G01N 27/44704; G01N 27/44743
See application file for complete search history.

(56) References Cited

U.S. PATENT DOCUMENTS

| | | |
|---|---|---|
| 2011/0005932 A1 | 1/2011 | Jovanovich et al. |
| 2015/0136604 A1 | 5/2015 | Nielsen et al. |
| 2016/0187293 A1 | 6/2016 | Zenhausern et al. |

FOREIGN PATENT DOCUMENTS

| | | |
|---|---|---|
| WO | 2018032043 A1 | 2/2018 |
| WO | 2018067976 A1 | 4/2018 |

* cited by examiner

APPARATUS AND METHOD FOR DETERMINATION OF BANNED SUBSTANCES

PRIORITY

This application is a continuation application of International Patent Application Number PCT/EP2020/074255 filed on Aug. 31, 2021, and claiming priority of U.S. provisional application 62/893,871 filed on Aug. 30, 2019, the contents of both of which are incorporated by reference herein in their entirety.

TECHNICAL FIELD

The present invention relates to systems and methods for the separation and detection of banned substances and more specifically to illegal drugs found in a suspect's biological fluid, in particular in oral fluid (saliva), but not limited to detection of explosives, toxic industrial chemicals and other banned or regulated compounds, biomarkers and phytochemicals in a sample in situ. The invention bases on the application of the miniaturized capillary electrophoresis (CE) for separation of target compounds combined with two detection technologies: either native fluorescence of those compounds using short wavelength excitation, in particular within 200 to 275 nm wavelength range, or detection of impedance of analytes, not limiting to simultaneous use of both detection technologies. The systems and methods have particular application in the analysis on the field to enable the detection of the existence banned or regulated chemicals typically present in e.g., street samples. The invention also relates to capillaries, chemicals, sample collection kits and uses associated with the systems and methods for carrying out the method and system.

BACKGROUND ART

Illegal drug use is a globally recognized phenomenon affecting thousands of victims every year. New illegal drugs are continuously coming to the market motivating society to search for tools to combat the production, trafficking, distribution and use of these illegal drugs. The use of drugs is found giving rise to many illegal activities that consume a lot of resources of the countries. Therefore, European Union, Norway, Australia, USA, Canada and other countries have already stringent laws for drug abuse and have mandated the drug testing.

Detection of illegal drugs can be broadly categorized into either non-confirmatory or confirmatory analysis. Non-confirmatory analysis deals with the analysis and identification of illegal drugs at the point where such chemicals have been presumably consumed. The confirmatory analysis is performed in the laboratory, which involves the identification of the use of drug by suspect with some kind of device and is employed in sample preparation, storage and transport to corresponding central lab using cargo entry points and secure facilities for transport. While both categories of detection are important, the preventative nature of confirmatory test on a site makes it extremely useful.

Generally, drug testing is conducted using urine, blood, sweat, hair or oral fluid (saliva). Urine provides retrospective information about past drug use but provide little information about the current effect of the drug on a person and/or their ability to drive. Blood and oral fluid (OF) are likely to give the most accurate measurement of an illegal drug's active form concentration, which is what affects driving behavior.

The analysis of oral fluid for illegal drug abuse determination offers different advantages compared to blood and urine. Nonmedical personnel can collect it in a simple, inexpensive, and non-invasive manner. Oral fluid sampling can be closely supervised without an invasion of privacy and to prevent substitution, adulteration, or dilution of the sample, which could happen with urine analysis. Oral fluid sampling also avoids the risk of infection, which is possible during a blood draw.

Several approaches for detecting drugs in OF have been developed. They can be categorized as non-confirmatory and confirmatory methods. The majority of non-confirmatory methods are used in situ and they are based on immunological procedures. The present immunoassay tests are simple and easy to use, but these kind of tests have high error rates due to the ambiguity of detection (in the form of faint stripes), degradation of antibodies used, and cross reactivity with other analytes. Some examples of the cross-reactivity are listed here: Remnants of poppy seed roll give false positive for heroin due to the morphine and codeine naturally found in poppy seeds, for example morphine and codeine concentrations are from 7 to 333 ng/mL and from 8 to 112 ng/mL, respectively, [Concentrations of Morphine and Codeine in Paired Oral Fluid and Urine Specimens Following Ingestion of a Poppy Seed Roll and Raw Poppy Seeds Kimberly L. Samano, Randal E. Clouette, Barbara J. Rowland, R. H. Barry Sample *Journal of Analytical Toxicology*, Volume 39, Issue 8, October 2015, Pages 655-661, https://doi.org/10.1093/jat/bkv081, Published: 16 Sep. 2015]. Ecstasy (MDMA) and its analogue MDEA cannot be differentiated from methamphetamine. Tyramine found naturally in OF metabolized by a monoamine oxidase (MAO) and/or coming from food (meat, fish, cheese, alcoholic beverages, and protein rich food) can give false positive for amphetamine testing. MDEA's and MDMA's metabolite MDA gives false positive for amphetamine, for example, cross-reactivity 100 ng/ml for Dräger Drug Test 5000, (Dräger DrugTest 5000 STK IVD User Manual Table 1 Specificity), Reference: Souza, Daniele & Boehl, Paula & Comiran, Eloisa & Prusch, Débora & Zancanaro, Ivomar & Fuentefria, Alexandre & Pechansky, Flavio & Duarte, Paulina & De Boni, Raquel & Fröehlich, Pedro. (2012). *Which amphetamine-type stimulants can be detected by oral fluid immunoassays. Therapeutic drug monitoring.* 34. 98-109. Noscapine and lidocaine give false positive for opiate test and helional for ecstasy test, Biosens 600, Performance Characteristics Biosens 600, Ed 4 (2014-05-21). The immunoassay tests would fall to identify poly-drug mixtures of amphetamine, MDMA, MDEA, MDEA and/or methamphetamine. According to the DRUID study performed during 2013-2015 in Spain, 42.7% of the samples tested contained two or more drugs.

This fact results to the situation that there is a great probability of obtaining a false negative or false positive result. Some studies performed with various commercially available assays revealed a 70% false positive and sometimes 50% false negative detection accuracy. Other independent case studies showed that the error for being punished while not using illegal drugs was 40-90% and error rates for not being punished while drugged was 50-100%, respectively. Moreover, these immunoassay tests are only qualitative and, therefore, cannot give an estimation of the impairment level neither the indication of the recent drug use. The immunoassay tests have certain non-adjustable cut off limits, varying from manufacturer to manufacturer. Therefore, when the 'per se' threshold approach is implemented, the threshold limits can be adjusted to the cut-off of immunoassay strips, not vice versa.

Other pitfalls of immunoassay tests are well known:
The high cost of immunoassay tests.
All immunoassay manufacturers recommend waiting 10 minutes until sample collection if the suspect has eaten, drunken, chewed or smoked before the test. This fact significantly increases the overall time of testing even up to 20-30 minutes per person.
"YES/NO" answer for immunoassay tests make the use of the existing tests problematic.
It is time-consuming or even sometimes impossible to collect enough OF for analysis due to the dry mouth effect while drug impaired.

Thus, immunoassays are used as preliminary screening approaches, in situ, which are then followed by a chromatographic technique to confirm the results. Well-known chromato-mass-spectroscopic methods like gas chromatography-mass spectrometry or liquid chromatography-mass spectrometry have been described for determination of banned chemicals. In comparison to the immunoassays, chromatographic techniques are not suitable for field analysis, in general, require sophisticated sample pre-treatment, qualified personal for performing measurements which makes the overall process of analysis time-consuming.

All the reasons above encourage and promote more and more attention to the development of alternative method approaches. Technological advancements and product portfolio expansion is the key trend witnessed in the market.

Implementation of robust, reproducible, user-friendly technology is critical to meet the testing suspects of using illegal drugs in situ (roadside, public events) placed on today's law enforcement institutions. Upgrades in technology are necessary to facilitate increased output, while continuing to generate quality analytical data and attempting to minimize the number of invalid test results and instrument-related investigations. It is desirable to achieve adequate resolution between analytes, and separations within reasonable timeframes, and with reliable reproducibility. The instrument and method must be robust and completely automatic so it could be operated by a layperson (e.g., a law enforcement officer). Thus, it is an object of the invention to provide improved illegal drug tester for using on the site but free of immunoassay pitfalls and thus, having confirmatory power.

There is considerable interest in the development of such fast and reliable analytical instrumentation for the identification of illegal drugs and other banned chemicals since the results provided by these analyses constitute an indispensable tool for law enforcement agencies during the investigations and prevention of use of illegal drugs and other banned chemicals. While electrophoresis has historically been used in quality control for product purity and fragmentation analysis, the methodology has transformed from gel-based, to capillary-based, and more recently, to the portable instruments. Capillary electrophoresis (CE) is alternative technology to immunoassay. It is, undoubtedly, one of the easiest methods to be miniaturized and automated. Portable capillary electrophoresis allows for dramatically reduced sample analysis times, while maintaining the performance and reproducibility standards required for forensic analysis, (Ryvolová, M., Macka, M. and Preisler, J., 2010. *Portable capillary-based (non-chip) capillary electrophoresis. TrAC Trends in Analytical Chemistry,* 29(4), pp. 339-353).

Until now, CE has received less attention as a tool for determination of illegal drugs. CE requires extremely low volumes of sample and is quick and cost-effective.

The small sample size and the small detection path length (25-75 µm) makes the detection limits of the CE several orders higher than in the case of other chromatographic and spectroscopic techniques. This, however, can be overcome by using advanced detection technologies such as fluorescence and impedance. One attractive feature of CE is the compactness and robustness of the equipment, which would open the opportunity for the construction of portable instruments. These could be used as a confirmation tool by law enforcement agencies in situ, at the point of interest (in street, roadside, public events). If the detection limits of the CE could be reduced to the required cut off level, then CE instruments could become an attractive alternative to the immunoassays.

In addition, uniqueness of CE includes:
new innovative technology, none on the market;
identifies not the class, but the illegal drug itself and shows concentration level even in poly drug mixtures: more selective than the commercially available tests;
no cross-reaction issue as for immunoassay;
the list of the detectable compounds can be expanded easier than for immunoassay tests;
the collected sample can be re-analyzed by confirmative method in lab. No need for the second sampling;
user friendly software for operator, automatic result generation;
the sample can be collected immediately even if the person ate, drunk, smoked within 10 minutes without interference;
dry mouth is not a problem due to the special sample collection procedure;
possibility to analyze illegal drugs in other sample matrices such as blood, urine, exhaled breath, plant materials, powders, pills, surfaces;
possibility to add new applications for food industry, biotechnology, environmental monitoring.

CE with native fluorescence detection capability offers an attractive combination having potential for the confirmatory identification of illegal drug consumption on the site. A portable, CE instrument with miniature flash Xe-lamp with excitation broadband from 200 to 275 nm have greater flexibility for detection of illegal drugs in suspected saliva which has been demonstrated at the several electronic music festival (in Estonia, between 2016 to 2019 years and roadside testing, (Saar-Reismaa, P., Erme, E., Vaher, M., Kulp, M., Kaljurand, M. and Mazina-Šinkar, J., 2018. *In situ determination of illegal drugs in oral fluid by portable capillary electrophoresis with deep UV excited fluorescence detection. Analytical Chemistry,* 90(10), pp. 6253-6258).

SUMMARY OF INVENTION

The present invention relates to roadside analyzer for determination of illegal drugs abuse, including, but not limiting to detection of explosives, toxic industrial chemicals and other banned or regulated compounds, biomarkers and phytochemicals in a sample in situ in at least one human body fluid sample, specifically in oral fluid (saliva), but not limiting to other clinical samples of interest (urine, blood, exhaled breath, exhaled breath condensate, etc.) It consists of automatic processor for preparing samples suitable for analysis. Analysis part of the instrument implements three technologies, namely solid phase extraction prior to analysis, capillary electrophoresis for separation of analytes from the sample matrix and impedance (contactless conductivity) or fluorescence or both impedance (contactless conductivity) and fluorescence for detection of analytes of interest. Contrary to the sensors based on the molecular recognition, analyzer identifies not the class of illegal drugs (e.g., "Amphetamines") but the illegal drug itself (e.g. amphetamine, methamphetamine, ecstasy (MDMA) and its analogues (MDA, MDEA, PMA, PMMA). It determines the use of other drugs like cocaine, marijuana cannabinoids (THC, CBD), LSD, morphine and others, including, but not limited to other drugs and banned or regulated compounds, and estimates their concentration in sample of interest, in particular in oral fluid (saliva sample) at the confidence needed for confirmatory power and can be used at the point of interest (street, roadside, public events). Performance of the analyzer is superior to commercially available testers (based on immunoassay) because it is more selective than those testers and gives more information regarding the real drugged level of alleged person and the recent use. The analyzer is simple enough to be used in the field and handled by various professionals (police, custom workers, prison guards and various transport situations).

The present invention provides highly sensitive and selective an illegal drug testing device for the separation, detection and quantification of banned compounds, specifically amphetamine, methamphetamine, MDMA, MDEA, MDA, cocaine, cocaethylene, morphine, codeine, LSD, fentanyl, not limiting to other banned compounds having native fluorescence within 285 nm to 600 nm while being excited at short wavelength excitation from 200 to 275 nm, in a sample of interest, specifically in an oral fluid, not limiting to other biological sample such as urine, blood, plasma, serum, exhaled breath, exhaled breath condensate, sweat, hair, etc., is provided, the device comprising

- a sample processing device for extraction of analytes from oral fluid,
- a carousel autosampler for injecting fluids including sample solutions and electrically conductive background electrolyte into an inlet end of the separation capillary,
- a high voltage power supply,
- a separation capillary or capillaries with filled background electrolyte,
- a fluorescence detector for detecting drugs, including illegal drugs (amphetamine, methamphetamine, MDMA (ecstasy), MDEA, MDA, cocaine, cocaethylene, fentanyl, heroin, morphine, LSD, psilocybin, MDPV, CPP, cannabinoids, BZP, TFMPP and other natively fluorescing compounds) that pass through a detection window or multiple detection windows of the separation channel,
- a built-in computer for controlling the injection system, flow of fluids, operation of the detector for the detection illegal drugs,
- a computer display providing a visual representation of the presence of illegal drugs in the sample. The combination of rapid separation and longer running duration makes the electrophoresis system suitable for automation and high sample throughput applications.

A confirmatory illegal drug device is provided for the separation and detection of γ-hydroxybutyric acid (GHB or "rape drug"), psilocybin, not limiting to other banned compounds, in a sample of interest, specifically in an oral fluid, not limiting to other biological sample such as urine, blood, plasma, serum, exhaled breath, exhaled breath condensate, sweat, hair, etc., is provided, the device comprising:

- a sample processing device for extraction of analytes from oral fluid,
- a carousel autosampler for injecting fluids including sample solutions and electrically conductive background electrolyte into an inlet end of the separation capillary;
- a separation capillary or capillaries with filled background electrolyte;
- a contactless conductivity detector for detecting GHB, and psilocybin that that pass through a detection window or multiple detection windows of the separation channel;
- a built-in computer for controlling the injection system, flow of fluids, operation of the detector for the detection illegal drugs,
- a computer display providing a visual representation of the presence of illegal drugs in the sample. The combination of rapid separation and longer running duration makes the electrophoresis system suitable for automation and high sample throughput applications.

A method is provided for the separation and detection of illegal drugs in a sample using electrophoresis, the method comprising a sample processing sequence which comprises:

- In case of dry mouth, rinsing of suspects mouth with mouth rinsing solution, most preferably 5 mL of physiological saline solution or deionized water for 30 seconds, not limiting to other volumes of mouth rinsing solution and/or duration time of rinsing step, and, thereafter, introducing of oral fluid-rinsing mouth solution into collection tube;
- introducing a tampon/swab/pad with suspects oral fluid into a vacuumed container to remove extra saliva;
- applying an extraction solvent to the tampon/swab to extract the analytes of interest from the tampon/swab; wherein extraction solvent comprises the suitable solvent, most preferably acetonitrile;
- directing the extract to the sample vial through the filter which removes peptides from the sample; wherein filter comprises unbound silica, including, but not limiting to other solid phases such as C18, etc. and
- introducing the vial with the sample to the analyzer with the help of peristaltic micropump.

The system comprises a fluid flow generator, such as a pump, for generating the flow of capillary conditioning liquid, background electrolyte (BGE) or sample through the injection system and capillary. The system comprises a built-in computer, which controls the injection system, flow of capillary conditioning liquid, BGE or sample through the injection system.

Abbreviations Used in Application

ACN—acetonitrile
AMP—amphetamine
BGE—background electrolyte
BTEX—refers to the chemicals benzene, toluene, ethylbenzene and xylene
BZP—benzylpiperazine
CE—capillary electrophoresis
CBD—cannabidiol
COC—cocaine
COET—cocaethylene
CPP—chlorophenylpiperazine
FD—fluorescence detection
GHB—γ-hydroxybutyric acid
LSD—lysergic acid diethylamide
MDA—3,4-methylenedioxyamphetamine MDEA—3,4-methylenedioxy-N-ethylamphetamine
MDMA—3,4-methylenedioxymethamphetamine, ecstasy
MDPV—methylenedioxypyrovalerone
MeOH—methanol
METH—methamphetamine
NACE—non-aqueous capillary electrophoresis
OF—oral fluid
PMA—p-methoxyamphetamine
PMMA—p-methoxymethamphetamine
PMT—photomultiplier tube
TEA—triethylamine
TFMPP—trifluoromethylphenylpiperazine
THC—tetrahydrocannabinol

BRIEF DESCRIPTION OF DRAWINGS

The invention is described in detail with references to the drawings where in

DESCRIPTION OF EMBODIMENTS

Figure 1:
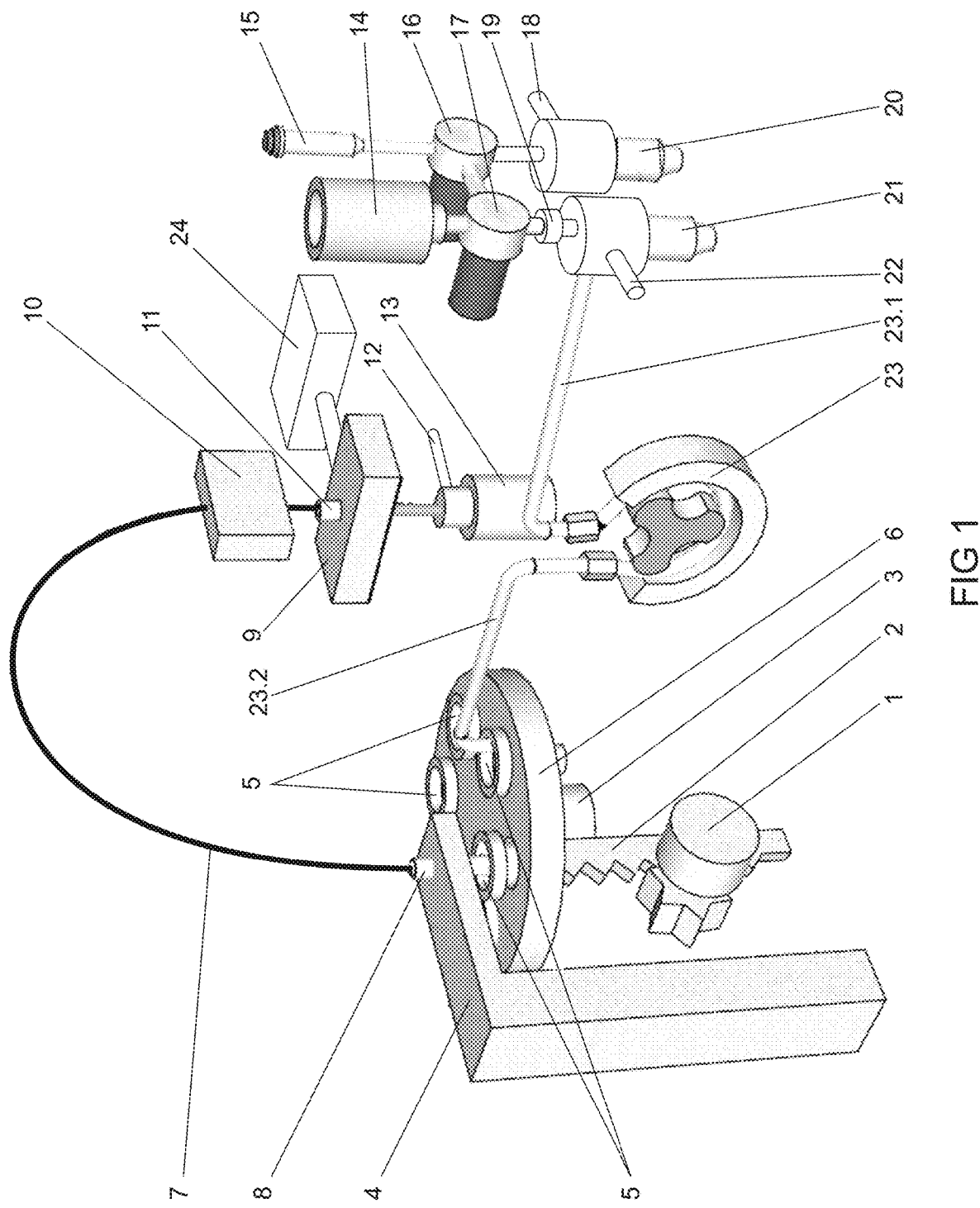
FIG. 1 is illustrated generally a functional schematic of the instrument.

The general concept of an apparatus according to the invention is illustrated in FIG. 1, where items 1 to 8 correspond to the analyzer sampler comprising a first stepper motor 1 controlling height of the lift of the vial, a vial lift 2, a second stepper motor 3, controlling the position of the sampler carousel, a stand 4 for the inlet electrode 8 and capillary 7 through the inlet electrode 8, an inlet vial 5, a sampler carousel 6, the separation capillary 7, the inlet electrode 8. The outlet part of the analyzer comprises outlet electrode 11, stand 9 for the outlet electrode 11 and capillary 7 passing through the electrode 11. The stand 9 is connected to BGE replenishment and rinsing system 24 and outlet vial 13. The first channel 12 connects the outlet vial 13 with the vacuum pump (not shown in drawings). The capillary 7 passes through fluorescence or impedance detector 10.

Sample extractor part comprises an extract vial 14, a syringe 15 for tampon/swab with collected sample of interest, a solenoid valve 16 for extra saliva removal, a solenoid valve 17 for directing extracted sample to a sample vial 21, a second channel 18 to vacuum pump (not shown in drawings), mentioned above second channel 18 connects a vial for extra saliva collection 20 to vacuum pump (not shown in drawings), a solid phase extractor 19, the vial for extra saliva collection 20, a sample vial 21, third channel 22 connecting to the sample vial 21 to vacuum pump (not shown in drawings), a micro peristaltic pump 23 connected via inlet conduit 23.1 to sample vial 21 and via outlet conduit 23.2 to inlet vial 5 for directing sample from sample vial 21 to inlet vial 5.

Figure 2:
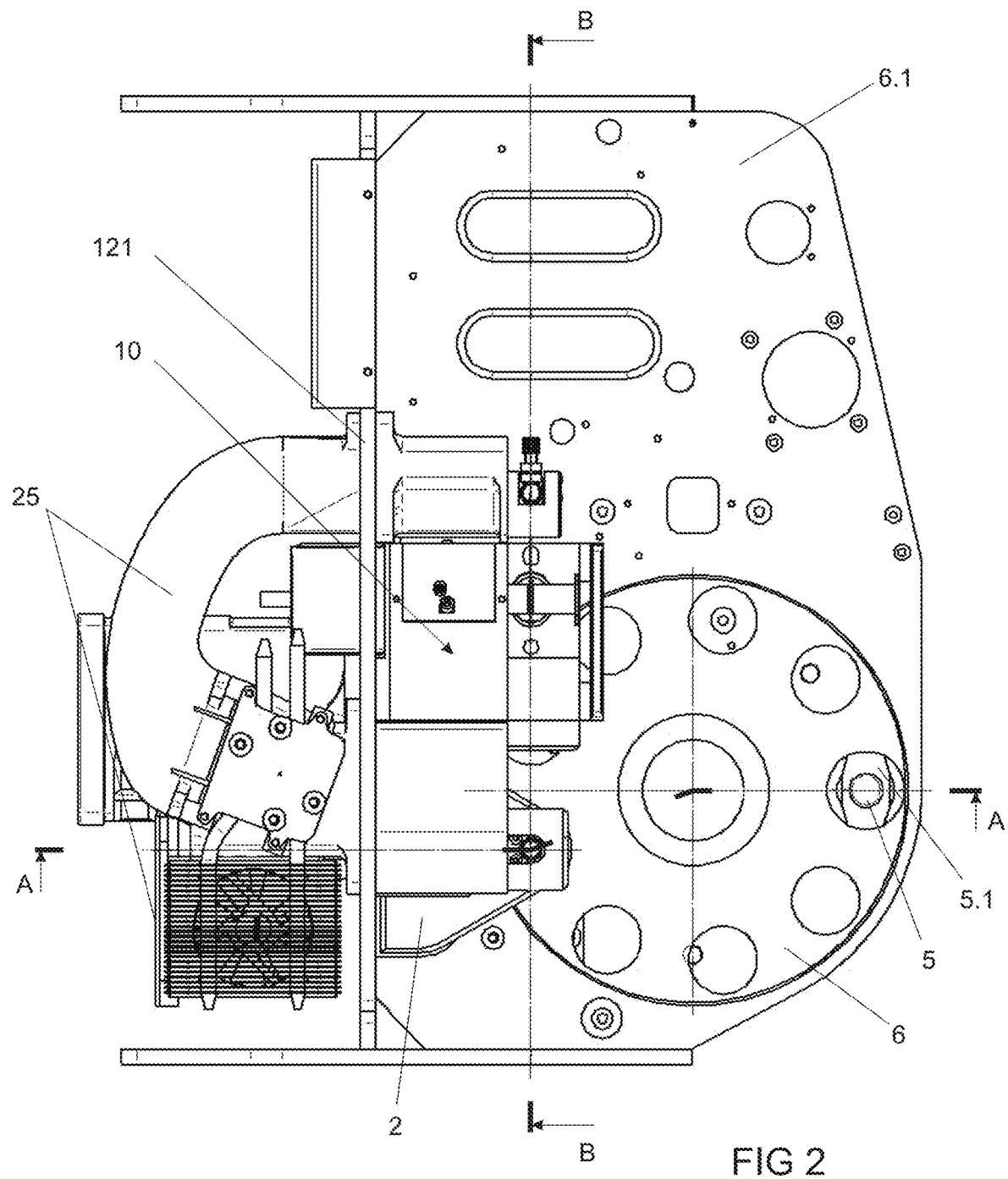
FIG. 2 is top view to the assembly of the apparatus according to present invention.

The assembly of the apparatus according to present invention (FIG. 2) comprises fluorescence detector 10 attached to the support frame 121 of the analyzer, a sampler carousel 6 with vial adapter 5.1 with vial 5, base of carousel 6.1, lift mechanism 2, cooling system using Peltier elements 25.

Figure 3:
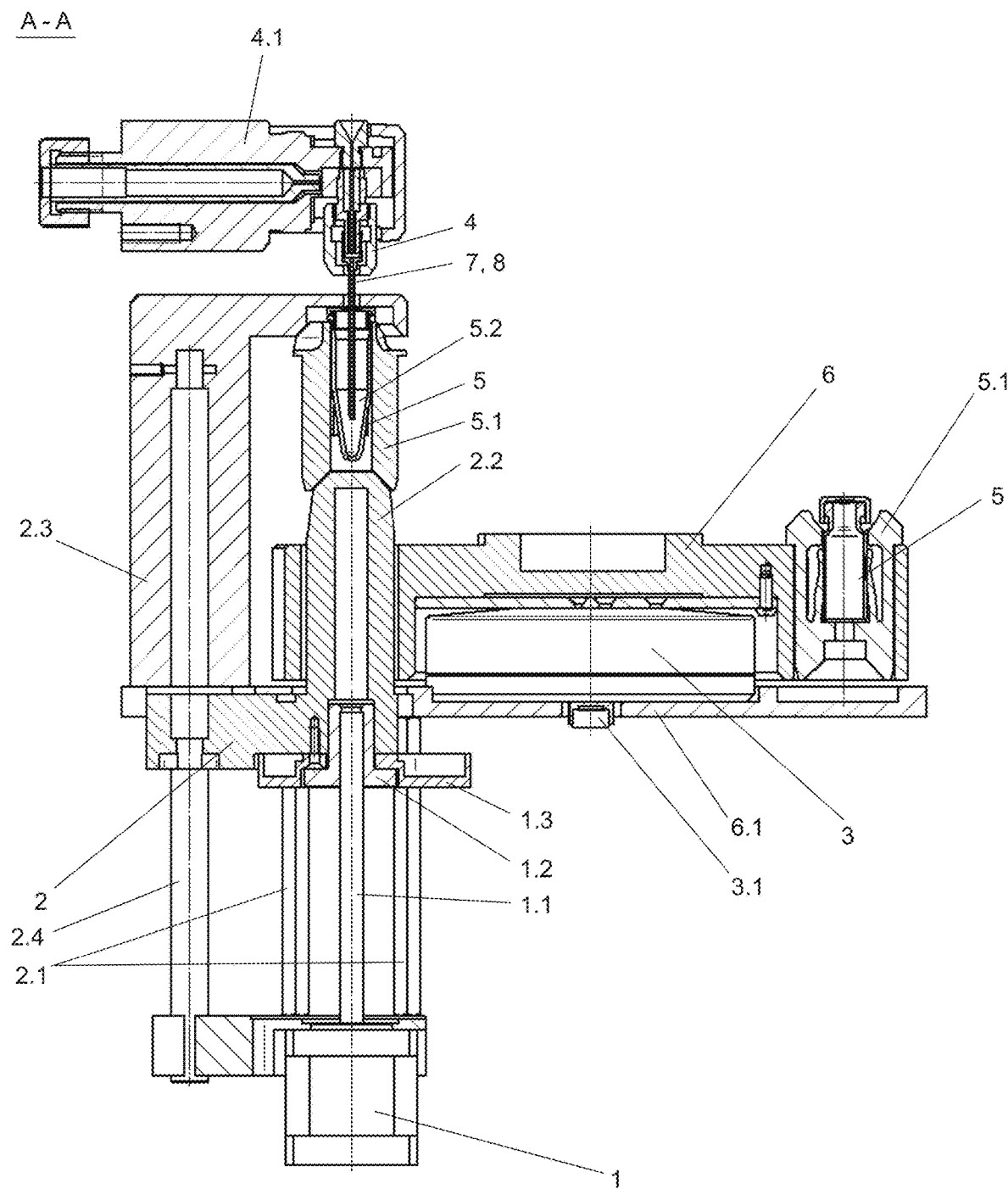
FIG. 3 is a cross section view along the line A-A in FIG. 2 to illustrate main details of the sample carousel according to embodiment of invention.
Figure 4:
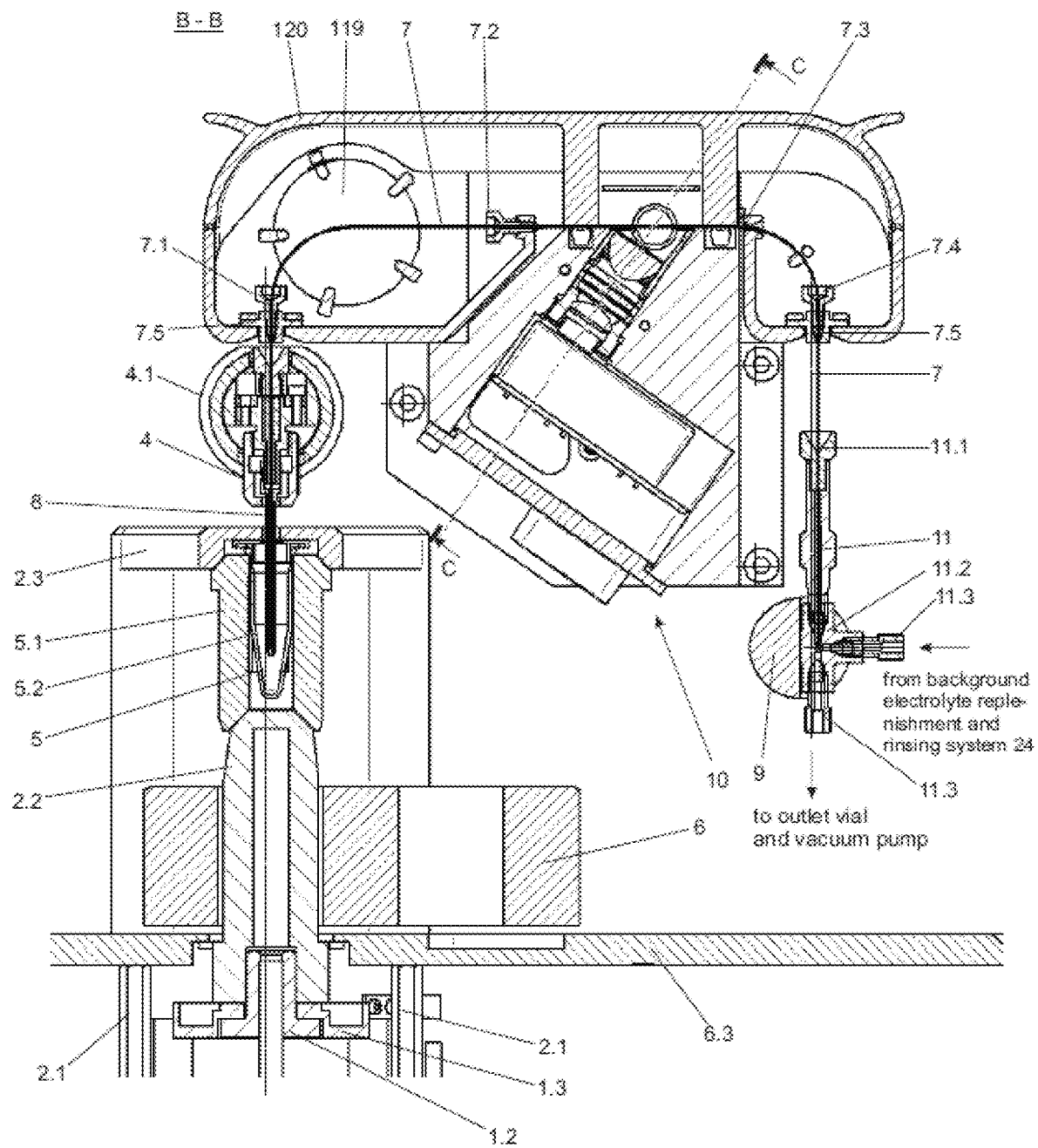
FIG. 4 is a cross section view along the line B-B in FIG. 2 to illustrate sample vial, separation capillary, capillary outlet and outlet electrode according to embodiment of invention.

The sample carousel (FIG. 3) according to embodiment of invention comprises the first stepper motor 1 for lifting vial 5. The stepper motor 1 is connected via shaft 1.1, connecting sleeve 1.2 and connecting plate 1.3 to the vial lift 2. The vial lift 2 comprises head of the lifting mechanism 2.2, which connects to the vial 5 located in vial adapter 5.1 to rise it to the level enabling electrode 8 with separation capillary 7 to be drawn into conditioning liquid 5.2 in vial 5. In addition, the lifting mechanism comprises supporting rods 2.1 for the lift stepper motor, linear guides 2.4 providing smooth vertical movement of the vial lift 2, Vial remover of lifting mechanism 2.3 removes the vial 5 from inlet electrode 8, keeping the vial against head of lifting mechanism 2.2. Inlet electrode 8 is mounted on the stand for the inlet electrode 4 and stand base 4.1. The separation capillary 7 (see drawing FIG. 4) is guided through capillary chamber 119 by capillary guides 7.1, 7.2, 7.3, 7.4, where first and last capillary guide 7.1 and 7.4 are attached to the housing of the capillary chamber 120 by connection elements 7.5. The capillary chamber 119 is closed with housing of the capillary chamber 120. The capillary chamber and fluorescence detector 10 are attached to the support frame 121 of the analyzer (shown in FIG. 5).

Figure 5:
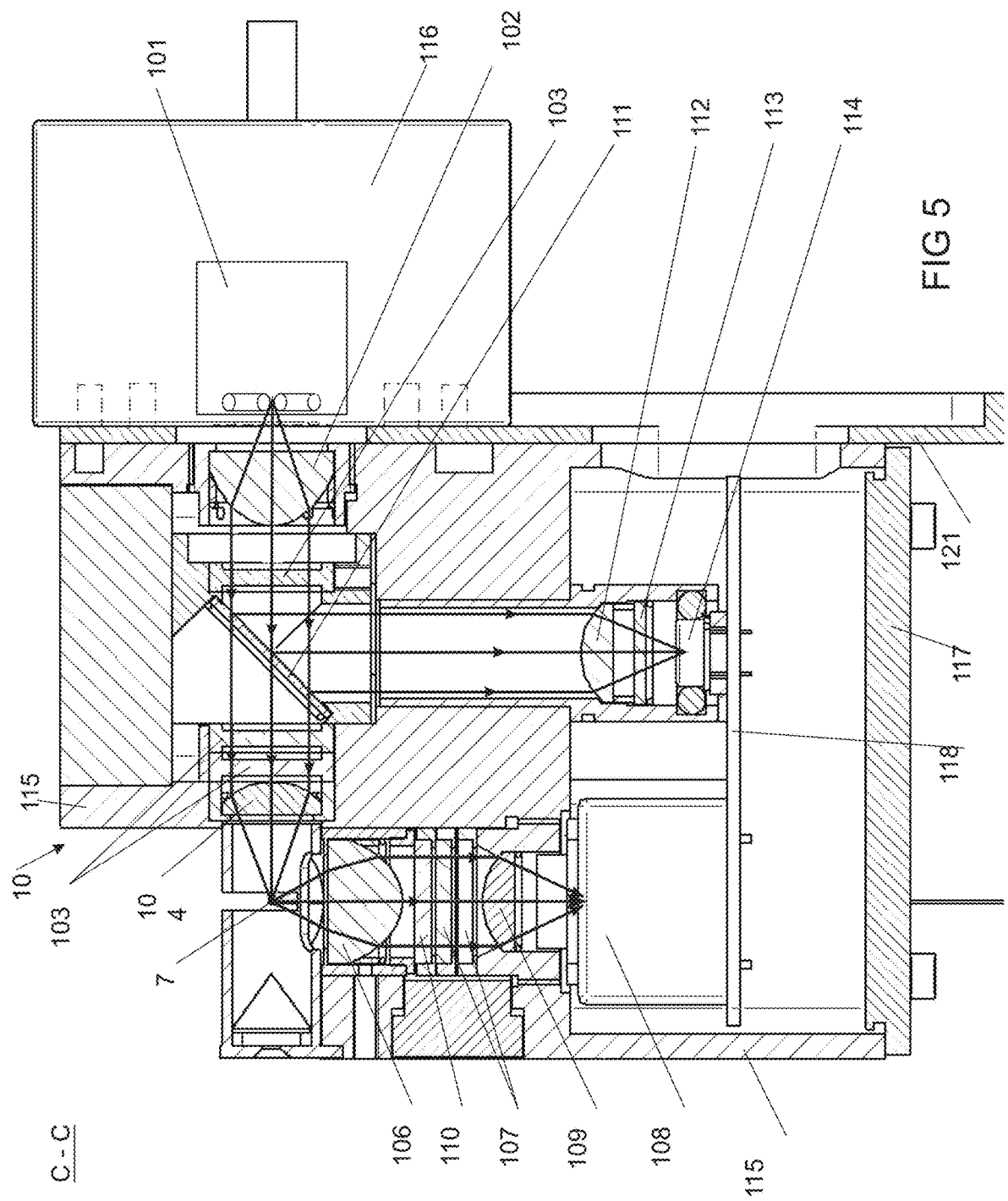
FIG. 5 is a cross section view along the line C-C in FIG. 4 to illustrate a schematic of the fluorescence detector according to embodiment of the invention.

In FIG. 5 is illustrated schematically fluorescence detector part of the apparatus according to invention, where a fluorescence detector 10 comprises a xenon lamp 101, aspherical collimator lens 102, excitation filters 103, excitation focusing lens 104, separation capillary 7, aspherical emission collecting lens 106, emission filters 107, a photomultiplier tube 108, emission focusing lens 109, a first neutral filter 110, a beam splitter 111, reference beam focusing lens 112, a second neutral filter 113, a reference photodiode 114.

Figure 6:
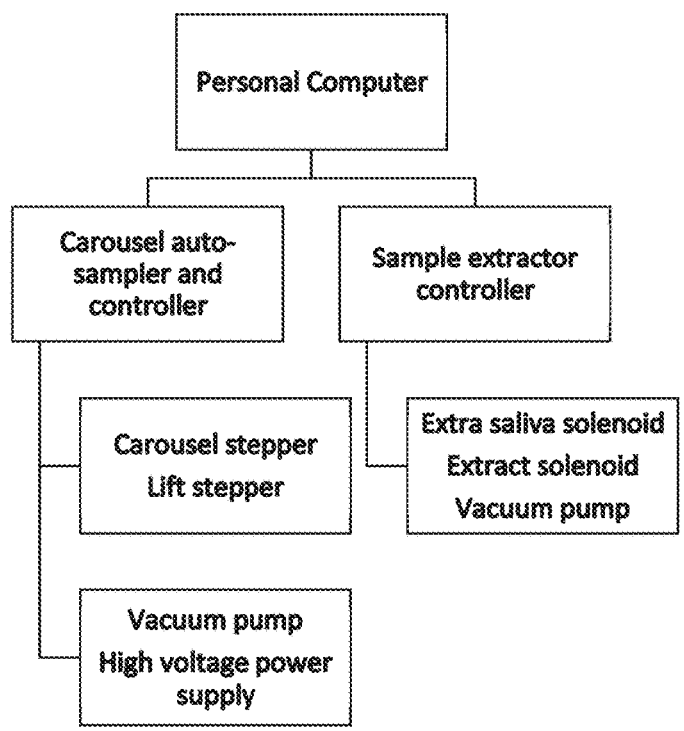
FIG. 6 illustrates the functional schematic of the device control according to invention.

The apparatus according to invention is controlled by computer (personal computer) via conventional connecting means (bluetooth, wi-fi, cable etc.) where in FIG. 6 is showed the functional schematic of the device control according to invention where computer program controls carousel auto-sampler and controller, carousel stepper with lift stepper, vacuum pump, and high voltage power supply to electrodes, sample extractor controller and extra saliva solenoid and vacuum pump.

Figure 7:
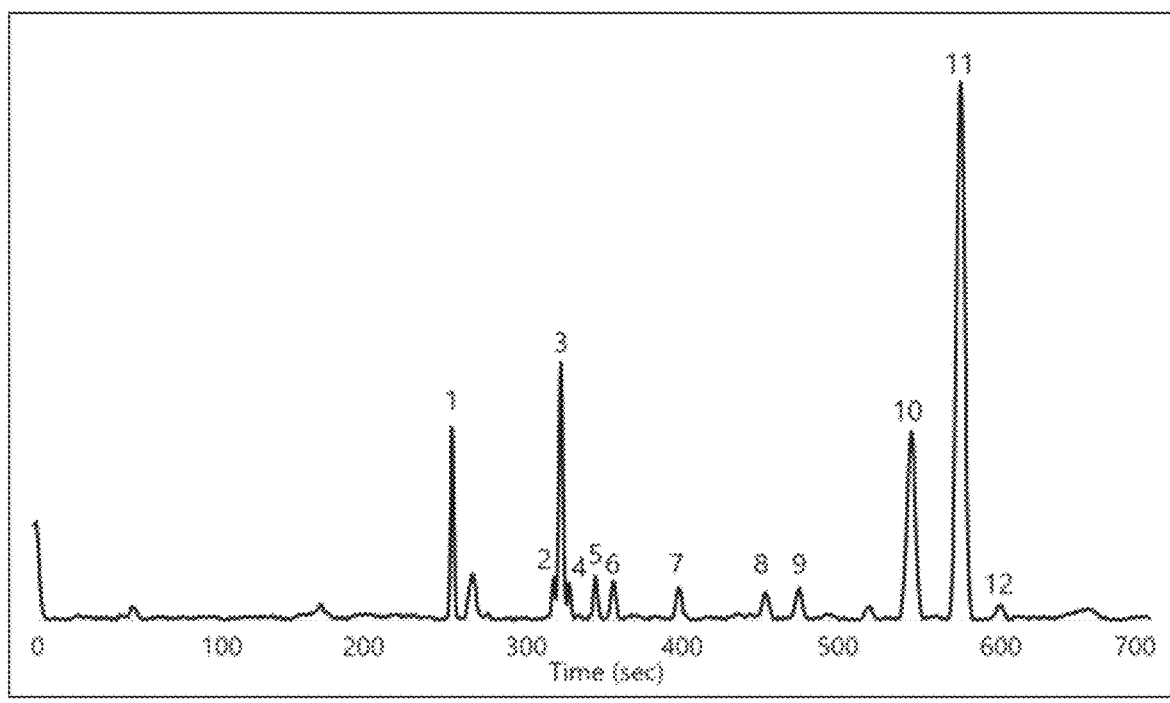
FIG. 7 is an example electropherogram of illegal drug standards for first method according to invention.

In FIG. 7 is an example electropherogram of illegal drug standards for first method according to invention. It is suitable for determination of amphetamine type stimulants and other common narcotics. Peak numbers in the figure correspond to the following Identified compounds: 1 and 10—internal standards, 2—AMP, 3—tyramine, 4—METH, 5—MDA, 6—MDMA, 7—MDEA, 8—cocaine, 9—cocaethylene (cocaine metabolite), 11—metoprolol (simulant of LSD) and 12—fentanyl.

Conditions: uncoated, fused-silica capillaries, i.d. 75 µm were used for the analyses. Fluorescence detector was positioned 35 cm to capillary end with total length of 51 cm. Prior to injection, the capillary was rinsed sequentially with 0.1 M NaOH, deionized water and the BGE for 2 min each. Separations were performed at +20 kV. Before the measurements, new capillaries were conditioned by rinsing them sequentially with 1 M sodium hydroxide and deionized water. Between analyses, the capillaries were rinsed with the BGE solution for 2 min.

Figure 8:
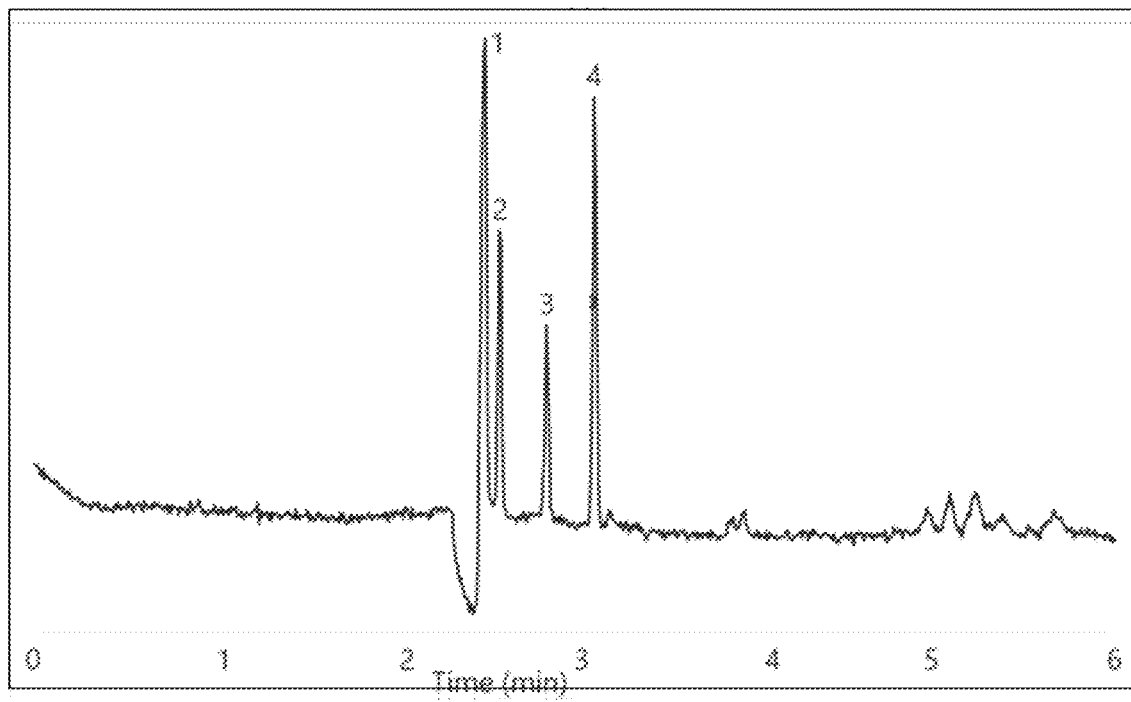
FIG. 8 is an electropherograms obtained for second method according to invention.

In FIG. 8 is an electropherograms obtained for second method according to invention. Capillary conditioning procedures are the same as described for FIG. 4. BGE2 was applied for analysis of cannabinoids. Peaks, 1—electroosmotic flow, 2—THC, 5—CBD, 4—internal standard.

Figure 9:
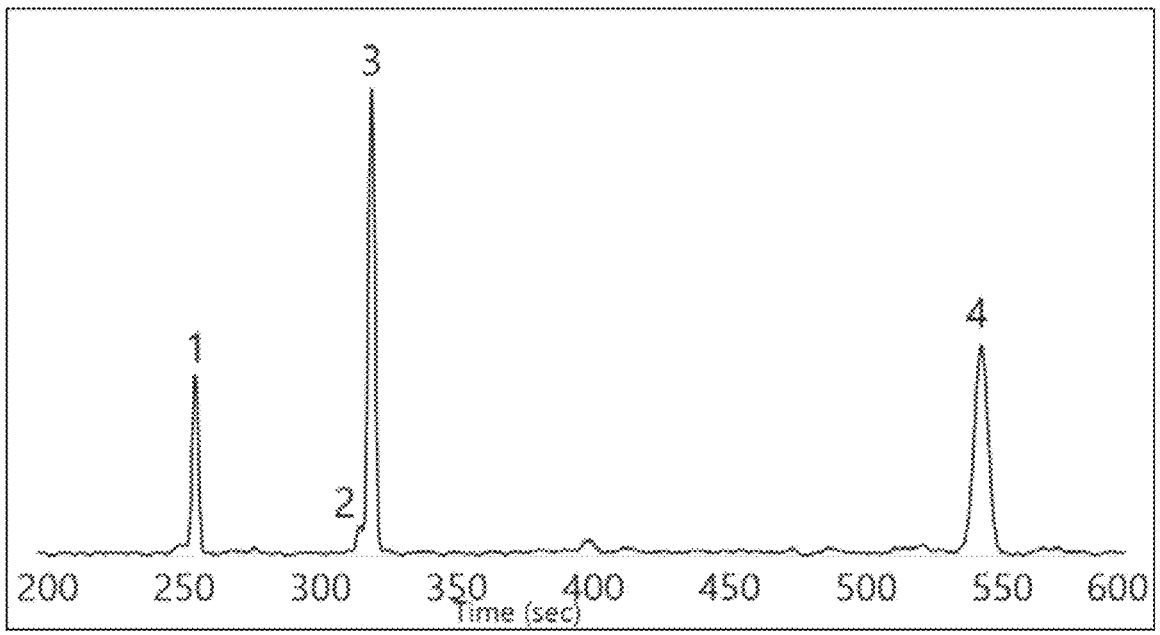
FIG. 9 illustrates a typical electropherograms of suspects' oral fluid samples.

In FIG. 9 is illustrated a typical electropherograms of suspects' oral fluid samples. The oral fluid samples were provided to us by police officers from the Police and Border Guard Board (PBG) of Estonia. The suspected users' OF sample contained 1 and 4—internal standards. 2—AMP and 3—tyramine (the compound is associated with smoking and some foods).

Portable CE Instrument.

The instrument consisted of a sample preparation unit (FIG. 1, elements 14-23) or without it (if manual sample preparation is performed), autosampler carousel (FIG. 1, element 6), separation capillary (FIG. 1, element 7), and detector (FIG. 1, element 10). During the analysis the electrodes (FIG. 1, element 8 and 11) are powered by high voltage power supply (not shown in drawings) and detector signal is recorded by built in computer. Built-in computer sends control signals to control board, which in turn controls stepper motors (FIG. 1, element 1 and 3), solenoid valves (FIG. 1, element 16, 17) and switches on/off the vacuum pump or pumps (not shown in drawings).

Sample Extraction Unit

The present device with methods can operate with automatic sample extraction unit (FIG. 1, elements 14-23) or without it. The work of the sample extraction unit is controlled by a built-in computer. Built-in computer sends control signals to control board, which in turn delivers commands to the solenoid valves and vacuum pump or pumps. Tampon/swab with suspect's oral fluid is placed into syringe 15 which is then sealed. Solenoid valve 16, which is initially in OFF position, allows excess saliva to be delivered into excess saliva vial 20 when the experiment starts after switching on the vacuum pump. Vacuum pump creates low pressure in the excess saliva vial 20. This facilitates removal of the superfluous saliva removed from the tampon/swab and retaining constant amount of sample into tampon/swab. After preset interval of time, the solenoid valve 16 is set to the ON position and because solenoid valve 17 is initially in OFF position the extractant in the vial 14 flows to the syringe 15 which retains low pressure. Sample is extracted from the tampon/swab, which is in the syringe 15, and during extraction atmospheric pressure establishes in the syringe 15. After preset time the solenoid valve is set ON position, which facilitates flow of extracted sample into sample vial 21 through the filter as solid phase extractor 19 due to the low pressure which has established there through third channel 22. Filter in solid phase extractor 19 removes peptides and proteins from the sample. When the transport of the sample to the sample vial 21 has been completed, the solenoids 16 and 17 are set to OFF position and vacuum pump is switched off. By initiating the work of the peristaltic pump 23 the sample is transported via inlet conduit 23.1 and outlet conduit 23.2 to the input vial 5 in the sampler carousel 6.

Carousel Autosampler

The work of the carousel autosampler unit (FIG. 1) is controlled by a built: in computer. Built-in computer sends control signals to control board, which in turn controls the lift stepper motor 1 and brushless DC motor 3 of carousel 6 and the vacuum pump (not shown in the drawings). Some of the input vials 5 in the carousel autosampler 6 are prefilled with capillary conditioning (wash) liquid and BGE, not limiting to other liquids, and the rest of the vials are filled with oral fluid extracts from the sample extraction unit or manually extracted samples.

1. Experiment starts by moving the vial 5 containing capillary conditioning liquid to the position under the electrode inlet 8 located in the stand 4. With the help of the vial lift 2 the stepper motor 1 rises the inlet vial 5 to the level which enables electrode 8 with separation capillary 7 to be drawn into conditioning liquid. The vacuum pump is switched ON and it creates low pressure in the output vial 13 through first channel 12. Due to the low pressure at the end of the separation capillary 7 the condition liquid flows through the capillary washing out impurities at the capillary inner wall and establishing permanent coverage of its inner surface with hydroxyl groups. The low pressure is set for the period, which enables to flow through the capillary amount of liquid equal to several volumes of inner volume of the capillary.
2. The procedure described in the p1 is repeated for the vial with BGE.
3. The procedure described in p1 is repeated for the vial, containing sample. However, now the capillary is only partially filled with sample at the inlet end.
4. High voltage is delivered to the inlet electrode 8 and outlet electrode 11.
5. During the electrophoresis run analytes pass before the detector window and are recorded by fluorescent detector 10.
6. After preset time the high voltage is switched off and all controls are reset.
7. For the following samples all the procedures 1-6 are repeated.

Fluorescence Detector.

Fluorescence detector 10 is shown in FIG. 5. The xenon flash lamp 101 in Xenon lamp housing 116 delivers 0.5 µs light pulses to the detection window of the separation capillary 7 at a repetition frequency of 300-700 Hz. An aspherical lens 102 is used to collect the excitation light and a spherical lens 104 to focus the light to the capillary 7 with high efficiency. The xenon flash lamp has strong emission bands in the region of 230-260 nm, but it emits also in the broad-spectrum range until near infrared. Therefore, a set of three bandpass filters or excitation filters 103 is used to block emission outside that region. Radiation emitted by the solution inside the capillary 7 is collected by an aspherical emission collecting lens 106 and focused by an emission focusing lens 109 on the cathode of the PMT 108, which is located perpendicularity to the excitation beam but at angle approximately of 55 degree to the capillary 7. This angle is introduced to minimize the intensity of the refracted and reflected in the capillary parasitic radiation from the Xenon lamp 101. Doubled emission filters 107 or first neutral filters 110 are mounted within 280-600 nm wavelength range for detection of analytes of interest, 280-340 nm wavelength range is useful for illegal drugs native fluorescence detection. An optical reference channel is introduced to eliminate the xenon lamp 101 aging effect on measurement accuracy. A beam splitter 111 reflects a part of the excitation beam and directs it through a reference beam focusing lens 112 to the reference photodetector or reference photodiode 114. A second neutral filter 113 is used to attenuate the reference flux. The reference signal is measured each time after turning on the detector, and its value was recorded in the memory and used for correction of measurement results.

Contactless Conductivity Detector

The fluorescence detector 10 can be replaced with other detectors of need, for example, the contactless conductivity detector. The cell of the contactless conductivity detector can have different designs. For instance, the cell can be built into a rectangular piece of alumina. Two tubular electrodes and an operational amplifier are placed inside the cage. Two tubular electrodes can have a length of 8 mm and a gap of 0.8 mm, not limiting to other sizes and materials. Electrodes are shielded from each other by the grounded conductive layer. One of the electrodes is excited with a voltage (60 V or different) peak-to-peak sine wave oscillating in a frequency range of 300 kHz-2 MHz (or different). The signal is picked up by the second electrode and further amplified. The software allows to control the hardware by changing the excitation frequency and amplification amount.

Background Electrolytes for Separation

A first method according to invention uses BGE1 which consisted of 95% (20 mM tris(hydroxymethyl) methylamine, 50 mM phosphoric acid, 0.4% triethylamine, pH 3.3) and 5% methanol as an organic modifier. Method 1 was used for separation of common narcotics (except THC and CBD). Example of separation is presented in the FIG. 7.

A second method according to invention implements nonaqueous capillary electrophoresis (NACE). It was used for the separation of THC and CBD cannabinoids. BGE2 consisted of 2.5 mM NaOH dissolved in MeOH/ACN (1:1) at pH=12. Example of separation is presented in the FIG. 8.

The background electrolyte composition is not limited to the compounds mentioned in method 1 and method 2.

EXAMPLES

To test the feasibility of the invention a prototype of the instrument was build. Details of the prototype are presented in FIG. 2-FIG. 5. The present invention will be first described by the following examples. These examples are provided to illustrate one mode for practicing the present invention and are not to be construed as limiting the scope of the invention as defined by the appended claims.

Performance Characteristics of Roadside Analyzer of Illegal Drugs

The specificity of the CE-FD analyzer was assured by the properly utilized excitation/emission filters in FD and which properties were suited to the native fluorescence characteristics of illegal drugs in the specific region under excitation within the wavelength range of 200-265 nm, not limiting to lower wavelength range up to 600 nm. Moreover, the specificity was achieved by utilized CE mode with the specific electrophoretic separation conditions and a special sampling/extraction/preconcentration procedure. Therefore, the probability of co-migrating of the fluorescing interference from another substance and their registering at the certain region of emission wavelength controlled by filters and CE conditions was minimized.

The instrumental detection (IDL) and quantification (IQL) limits of the illegal drugs were evaluated in acetonitrile using developed and optimized CE methodologies, excluding the matrix effect of OF and sampling/extraction/pre-concentration procedure recoveries. The instrumental detection and quantitation limits were found using the signal-to-noise (S/N) approach. The S/N ratio for IDL level equaled 3:1, proving the presence of the analyte in the test sample with a probability larger than 99%. The S/N ratio for IQL level was set to 10:1, respectively. The analysis of samples containing the analytes at the level of IDL was performed and the results showed that the designed CE-FD instrument was able to detect amphetamine, methamphetamine, MDMA, MDA, MDEA, cocaine, cocaethylene, fentanyl, morphine, LSD, THC and other illegal drugs and banned or regulated compounds at the recommended by DRUID project cut-off limits for illegal drug abuse determination in oral fluid.

Analysis of Oral Fluid Samples.

The assembly of the apparatus according to present invention is utilized for the determination of illegal drugs of abuse in OF during police roadside drug testing and at various public events (for example, music festivals). FIG. 9 presents the OF sample with drugs intoxication evidence.

LIST OF DETAILS

1—stepper motor controlling height of the lift of the vial
 1.1—shaft of the stepper motor
 1.2—connecting sleeve
 1.3—connecting plate
2—vial lift
 2.1—supporting rod for lifting mechanism
 2.2—head of lifting mechanism
 2.3—vial remover of lifting mechanism
 2.4—linear guides of lifting mechanism
3—brushless DC motor motor controlling the position of sampler carousel
 3.1—carousel position feedback magnet
4—stand for the inlet electrode
 4.1—base of the stand
5—inlet vial
 5.1—vial adapter
 5.2—sample
6—sampler carousel
 6.1—base of carousel
7—separation capillary or set of capillaries
 7.1, 7.2, 7.3, 7.4—capillary guide
 7.5—connection element for capillary guide
8—inlet electrode
9—stand for the outlet electrode and capillary through the electrode
10—fluorescence detector
 101—Xe lamp
 102—aspherical collimator lens
 103—excitation filters
 104—excitation focusing lens
 106—aspherical emission collecting lens
 107—emission filters
 108—photomultiplier tube (PMT)
 109—emission focusing lens
 110—first neutral filter
 111—beam splitter
 112—reference beam focusing lens
 113—second neutral filter
 114—reference photo diode
 115—housing of the detector
 116—housing of Xenon lamp
 117—cover of the detector housing
 118—circuit board for Xenon lamp, PMT, photo detector and other electronics
 119—capillary chamber
 120—cover of the capillary chamber
 121—support frame of analyzer
11—capillary outlet and outlet electrode
 11.1—capillary guide in outlet electrode
 11.2—outlet chip
 11.3—tube fitting
12—first channel to vacuum pump 13—outlet vial
14—extract vial
15—syringe for tampon/swab with collected sample of interest
16—first solenoid valve for extra saliva removal
17—second solenoid valve for directing extracted sample
18—second channel to vacuum pump
19—solid phase extractor
20—vial for extra saliva collection
21—sample vial
22—third channel to vacuum pump
23—micro peristaltic pump
23.1—inlet conduit from sample vial to peristaltic pump 23
23.2—outlet conduit from peristaltic pump to sample vial 5
24—BGE replenishment and rinsing system
25—cooling system using Peltier elements

What is claimed is:

1. An apparatus for the separation and determination of regulated compounds in biological fluid sample using electrophoresis and comprising
    at least one separation capillary;
    at least one fluorescence detector for characterizing electrophoretic zones of compounds passing through a detection zone of the at least one separation capillary;
    an injection system for introducing fluids, including sample solutions and background electrolyte into an inlet end of the at least one separation capillary, to conduct a sample processing sequence prior to a sample analysis sequence;
    a high voltage power supply;
    a computerized system for commanding the injection system, flow of fluids through the at least one separation capillary, and operation of the at least one fluorescence detector;
    a sample preparation and extraction device for processing a biological fluid sample, the device comprising a compartment for swab/pad/tampon comprising the biological fluid sample, vials for collecting excess oral fluid and sample solution, solenoid valves for controlling transport of the biological fluid sample through the device vessel containing extractant, a computerized controlling system for commanding the solenoid valves that facilitate flow of fluids through the separation channel, to conduct the sample processing sequence;
    the apparatus being configured to conduct the sample analysis sequence after conducting the sample processing sequence, wherein the sample analysis sequence comprises introduction of a sample and a background electrolyte and applying a voltage potential across the at least one separation capillary to effect separation of the compounds.

2. The apparatus according to claim 1, wherein the apparatus comprises at least one contactless conductivity detector.

3. The apparatus according to claim 1, wherein the apparatus comprises multiple fluorescence detectors.

4. The apparatus according to claim 1, wherein the apparatus comprises multiple contactless conductivity detectors.

5. The apparatus according to claim 1, wherein the apparatus comprises multiple fluorescence and contactless conductivity detectors.

6. The apparatus according to claim 1, wherein the apparatus comprises a temperature control system for temperature stabilization in a capillary chamber.

7. The apparatus according to claim 1 for detection of natively fluorescing compounds in a wavelength range from 220 nm to 600 nm, the compounds being selected from a group consisting of amphetamine, methamphetamine, MDMA (ecstasy), MDEA, MDA, cocaine, cocaethylene, fentanyl, heroin, morphine, LSD, psilocybin, MDPV, CPP, cannabinoids, BZP, TFMPP phenolic compounds, BTEX, and naphthalene derivatives.

8. The apparatus according to claim 1, wherein the biological sample is oral fluid, exhaled breath condensate, tears, hair, sweat, urine or blood sample.

9. The apparatus according to claim 1, wherein the biological sample is oral fluid, exhaled breath condensate, tears, hair, sweat, urine or blood sample.

10. A method for preparation of a biological sample for separation and determination of regulated compounds with the apparatus of claim 5, the method comprising the steps of:
    rinsing of a subject's mouth with 2-5 mL of mouth rinsing solution, physiological saline solution or deionized water for 30-60 seconds;
    introducing a mixture of oral fluid and mouth rinsing solution into a collection compartment and introducing a swab/pad/tampon into the compartment to be in contact with the mixture;
    introducing the tampon/swab/pad comprising the mixture into a vacuum container;
    applying extraction solvent to the tampon/swab/pad to extract compounds of interest;
    directing the extract to a sample vial through a solid phase extraction filter comprising unbound silica
    for removal of interfering peptides and proteins; and
    introducing the sample to apparatus of claim 5 with help of a peristaltic micropump.

11. The apparatus according to claim 1 wherein in the injection system the background electrolyte is water-based or based on a mixed aqueous-alcoholic solution including mineral acids organic acids.

12. The apparatus of claim 11 wherein the apparatus is suitable for determination of compounds selected from the group consisting of AMP, METH, MDMA, MDA, MDEA, PMA, and PMMA, cocaine and its metabolite cocaethylene, fentanyl, LSD, metoprolol, and morphine.

13. The apparatus according to claim 1, wherein the apparatus is configured to separate cannaboids by use of non-aqueous capillary electrophoresis (NACE) and wherein suitable organic solvents used for capillary electrophoresis-have high relative permittivity, so that the number density of charge carriers is given directly by the nominal concentration of the electrolyte, and such solvents include acetonitrile and methanol in which the analytes are dissociated.

14. The apparatus according to claim 13, wherein the background electrolyte comprises strong bases selected from sodium or potassium hydroxide dissolved in mixture of organic solvents.

* * * * *